United States Patent
Field (10) Patent No.: US 6,737,054 B2
(45) Date of Patent: *May 18, 2004

(54) MYOCARDIAL GRAFTS AND CELLULAR COMPOSITIONS USEFUL FOR SAME

(75) Inventor: Loren J. Field, Indianapolis, IN (US)

(73) Assignee: Advanced Research and Technology Institute, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/878,020

(22) Filed: Jun. 8, 2001

(65) Prior Publication Data

US 2002/0061295 A1 May 23, 2002

Related U.S. Application Data

(60) Continuation of application No. 09/441,315, filed on Nov. 16, 1999, which is a continuation of application No. 08/976,278, filed on Nov. 21, 1997, now Pat. No. 6,015,671, which is a continuation of application No. 08/477,783, filed on Jun. 7, 1995, now Pat. No. 5,733,727, which is a division of application No. 08/153,664, filed on Nov. 16, 1993, now Pat. No. 5,602,301.

(51) Int. Cl.$^7$ .............................. C12N 5/06; C12N 5/08
(52) U.S. Cl. ....................... 424/93.7; 435/325; 435/366
(58) Field of Search ........................... 424/93.7, 93.21, 424/97.7; 435/325, 366; 514/44

(56) References Cited

U.S. PATENT DOCUMENTS

| 5,103,821 A | 4/1992 | King | 607/9 |
|---|---|---|---|
| 5,602,301 A | 2/1997 | Field | |
| 2001/0038837 A1 | 11/2001 | Field | 424/93.7 |

FOREIGN PATENT DOCUMENTS

| WO | WO 94 24274 A | 10/1994 | C12N/15/00 |

OTHER PUBLICATIONS

Verma et al., Nature, vol. 389, Sep. 18, 1997, pp. 239–242.*
Anderson, Nature, vol. 392, Apr. 30, 1998, pp. 25–30.*
Bader, David et al.:"Repair and Reorganization of Minced Cardiac Muscle in the Adult Newt (*Notophthalmus viridescens*)", J. Morph., vol. 155, (1978) pp. 349–358.
Chiu, Ray C.–J. et al.:"Cellular Cardiomyoplasty: Myocardial Regeneration with Satellite Cell Implantation" Ann Thorac Surg, 1995; vol. 60, pp12–18.
Dorfman, Julia et al.:"Myocardial Tissue Engineering with Autologous Myoblast Implantation" The Journal of Thoracic and Cardiovascular Surgery, vol. 116, No. 5, pp 744–751.
Jain, Mohit et al.:"Cell Therapy Attenuates Deleterious Ventricular Remodeling and Improves Cardiac Performance After Myocardial Infarction", Circulation, Apr. 10, 2001, pp. 1920–1927.
Jockusch, Harold et al.:"Long–Term Expression of Isomyosins and Myoendocrine Functions in Ectopic Grafts of Atrial Tissue" Proc. Natl. Acad. Sci. USA, vol. 83, Oct. 1996, pp 7325–7329.

Kao, R.L. "Myoblast Implantation for Myocardial Regeneration: A Personal Odyssey" Cardiac and Vascular Regeneration, Sep. 2000, vol. 1, No. 3, pp. 211–213.
Kitsis, Richard N. et al.: "Hormonal Modulation of a Gene Injected into a Rat Heart In Vivo" PNAS, vol. 88, May 1991, pp 4138–4142.
Koh, Gou Young et al.:"Long Term Survival of AT–1 Cardiomyocyte Grafts in Syngeneic Myocardium" American Journal of Physiology, vol. 264, No. 5, Part 2, Jan. 1, 1993, pp H1727–H1733.
Koh, Gou Young et al.:"Differentiation and Long–Term Survival of C2C12 Myoblast Grafts in Heart" Journal of Clinical Investigation 1993, vol. 92, No. 3, Sep. 1993, pp 1548–1554.
Klug, M.G. et al.:"Genetically Selected Cardiomyocytes from Differentiating Embryonic Stem Cells Form Stable Intracardiac Grafts" Journal of Clinical Investigation, vol. 98, No. 1, Jul. 1, 1996, pp 216–224.
Marelli, D. et al., "Satellite Cell Implantation for Neomyocardial Regeneration" Transplantation Proceedings, vol. 24, No. 6 (Dec.), 1992, p. 2995.
Marelli, Daniel et al.:"Cell Transplantation for Myocardial Repair: An Experimental Approach" Cell Transplantation, vol. 1, 1992, pp 383–390.
Menasche, Philippe et al.:"Myoblast transplantation for Heart Failure" The Lancet, vol. 357, Jan. 27, 2001, pp 279–280.
Murry, Charles E. et al.:"Skeletal Myoblast Transplantation for Repair of Myocardial Necrosis" J. Clin. Invest., Dec. 1, 1996, vol. 98, No. 11, pp 2512–2523.
Reinecke, Hans et al.:"Skeletal Muscle Stem Cells Do Not Transdifferentiate Into Cardiomyocytes After Cardiac Grafting" J. Mol. Cell. Cardiol., Feb. 2002, vol. 34, No. 2, pp 241–249.
Reinecke, Hans, et al.:"Electromechanical Coupling Between Skeletal and Cardiac Muscle: Implications for Infarcet Repair" J. Cell. Biol., May 1, 2000, vol. 149, No. 3, pp 731–740.
Reinlib, L. et al. "Cell Transplantation as a Future Therapy for Cardiovascular Disease?: A Workshop of the National Heart, Lung, and Blood Institute" Circulation: Journal of the American Heart Association, vol. 101(8), May 9, 2000, pp e182–e187.
Shen, Sanbing et al.:"Embryonic Stem Cells Stably Transfected with mRARβ$_2$–lacZ Exhibit Specific Expression in Chimeric Embryos" Int. J. Dev. Biol., vol. 36, 1992, pp 465–476.

(List continued on next page.)

Primary Examiner—James Ketter
(74) Attorney, Agent, or Firm—Woodard, Emhardt, Moriarty, McNett & Henry, LLP (57) ABSTRACT

Described are preferred myocardial grafts of skeletal myoblasts or cardiomyocytes, and cellular compositions and methods useful in obtaining the grafts. The myocardial grafts are stable and can be used, for example, to deliver recombinant proteins directly to the heart.

15 Claims, 1 Drawing Sheet

OTHER PUBLICATIONS

Spring, K.J. et al.: "*Escherichia coli* GPT as a Positive and Negative Selectable Marker in Embryonal Stem Cells" Biochimica et Biophysica Acta 1218, 1994, pp 158–162.

Kao et al. "Satellite Cells for Myocardial Regeneration" Physiologist, 32:220, 1989.

Kao et al. Muscle Regeneration of Injured Myocardium, J. Cell , Biochemistry Suppl., 15C:73, 1991.

Marelli et al. "Satellite Cell Implantation for Neo–Myocardial Regeneration" Cell Transplantation, vol. I, Abstract No. 197 (First International Congress of The Cell Transplant Society May 31–Jun. 3, 1992).

* cited by examiner

Fig. 1

MYOCARDIAL GRAFTS AND CELLULAR COMPOSITIONS USEFUL FOR SAME

REFERENCE TO RELATED APPLICATIONS

This is a continuation of U.S. patent application Ser. No. 09/441,315 filed on Nov. 16, 1999, still pending; which is a continuation of U.S. patent application Ser. No. 08/976,278 filed Nov. 21, 1997, now U.S. Pat. No. 6,015,671 issued Jan. 18, 2000; which is continuation of U.S. patent application Ser. No. 08/477,783 filed Jun. 7, 1995, now U.S. Pat. No. 5,733,727 issued Mar. 31, 1998; which is a divisional of U.S. patent application Ser. No. 08/153,664 filed Nov. 16, 1993, now U.S. Pat. No. 5,602,301 issued Feb. 11, 1997.

This invention was made with government support under Grant Numbers HL 45453 and HL 61631 awarded by the National Institutes of Health. The government has certain rights in the invention.

BACKGROUND OF THE INVENTION

The present invention resides generally in the field of cardiology, and more particularly relates to stable myocardial grafts and methods and cellular compositions useful for achieving such grafts.

As further background, organ transplantation has been widely used to replace diseased, nonfunctional tissue. More recently, cellular transplantation to augment deficiencies in host tissue function has emerged as a potential therapeutic paradigm. One example of this approach is the well publicized use of fetal tissue in individuals with Parkinsonism (reviewed in (1), see reference list, infra.), where dopamine secretion from transplanted cells alleviates the deficiency in patients. In other studies, transplanted myoblasts from-uneffected siblings fused with endogenous myotubes in Duchenne's patients; importantly the grafted myotubes expressed wild-type dystrophin (2).

Despite their relevance in other areas, these earlier studies do not describe any cellular transplantation technology which can be succesfully aplied to the heart, where the ability to replace damaged myocardium would have obvious clinical relevance. Additionally, the use of intra-cardiac grafts to target the long-term expression of angiogenic factors and ionotropic peptides would be of therapeutic value for individuals with myocardial ischemia or congestive heart failure, respectively.

In light of this background there is a need for the development of cellular transplantation technology in the heart. Desirably, such technology would not only provide stable grafts in the heart but also enable the delivery of useful recombinant proteins or other molecules directly to the heart. The present invention addresses these needs.

SUMMARY OF THE INVENTION

The applicant has established cellular grafts in the myocardium which are viable long-term. Cardiomyocytes and skeletal myoblasts have been grafted directly into the myocardium of syngeneic animals. Viable grafts were detected at least one-half year post-implantation (the latest time point assayed). The presence of the grafts was not accompanied by overt cardiac arrhythmia, and the majority of the grafts were juxtaposed directly to the host myocardium and not encapsulated. It has thus been discovered that the myocardium can serve as a stable platform for cellular transplants. These transplants can be used for the local delivery of recombinant molecules to the heart and/or for replacing diseased tissue to supplement myocardial function.

Accordingly, one preferred embodiment of the invention provides a myocardial graft in an animal which includes a stable graft of skeletal myoblasts or cardiomyocytes incorporated in myocardial tissue of the animal.

Another preferred embodiment of the invention provides a method for forming a stable myocardial graft in an animal. The inventive method includes the step of introducing skeletal myoblasts or cardiomyocytes in myocardial tissue of the animal so as to form a stable myocardial graft. The cells can be conveniently introduced, for example, by injection.

Another preferred embodiment of the invention provides a method for delivering a recombinant molecule to myocardial tissue of an animal. This method includes the step of establishing a stable graft of skeletal myoblasts or cardiomyocytes incorporated in myocardial tissue of the animal, wherein the myoblasts or cardiomyocytes deliver the recombinant molecule to the myocardial tissue. In this embodiment the myoblasts or cardiomyocytes will carry transgenes encoding the recombinant molecule.

Another preferred embodiment of the invention provides a cellular composition comprising a substantially homogeneous population of non-immortalized cardiomyocytes. This and other cell populations can be obtained utilizing a preferred inventive method that includes (i) transfecting embryonic stem cells to introduce a marker gene enabling selection of one cell lineage from other cell lineages resulting from differentiation of the stem cells, (iii) causing the stem cells to differentiate, and (iv) selecting said one cell lineage based on the marker gene. The cells used in and resulting from such methods also form a part of the present invention.

Still another preferred embodiment of the invention provides a non-human animal having a stable graft of skeletal myoblasts or cardiomyocytes incorporated in myocardial tissue of the animal.

The invention thus provides myocardial grafts, methods and cellular compositions useful for forming myocardial grafts, and animals which have the myocardial grafts. The grafts will find use both as a vehicle for delivering therapeutic substances such as recombinant proteins and other molecules, and as a means for replacing diseased tissue to supplement myocardial function. Cellular compositions of the invention can be used directly to prepare grafts, and will also be useful in screening drug substance effects on cardiomyocytes and for expressing and obtaining recombinant proteins. Grafted animals can be used, for example, to screen the effects of recombinant molecules on the heart.

These and other objects and advantages of the invention will be be apparent from the following description.

DESCRIPTION OF THE PREFERRED EMBODIMENT

For the purpose of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention relates.

As indicated above, the present invention provides stable myocardial grafts of skeletal myoblasts and/or cardiomyocytes. In this regard, as used herein the term "stable myocardial graft" is intended to mean a myocardial graft whose cells are viable for a period of at least about 2 weeks. Surprisingly, such stable grafts have been readily achieved in accordance with the invention, with preferred grafts having cells viable for six months or more. Myocardial grafts of the invention can thus provide for long-term delivery of recombinant proteins or other molecules to the heart and/or long-term supplementation of myocardial tissue.

The skeletal myoblasts and cardiomyocytes used in the invention can be obtained or isolated from any suitable source. Skeletal myoblasts, including for example C2C12 skeletal myoblasts, are available from public depositories such as the American Type Culture Collection (ATCC) (Rockville, Md.). Skeletal myoblasts can also be isolated from skeletal muscle using techniques well known to the art and literature. Cardiomyocytes useful for the invention can be obtained using techniques described in the literature (3) or using methods described more particularly in the Examples below. Briefly, one such method involves digestion of heart tissues to obtain cardiomyoctes.

Another method involves using an appropriate marker to select specific cell lineages, such as cardiomyocytes, from other cell lineages resulting from the differentiation of embryonic stem cells (totipotent cell lines derived from the inner cell mass of blastocysts as described in (22)). The preferred method involves a positive selection scheme. Thus, a marker gene, such as a gene conferring antibiotic resistance (e.g. neomycin or hygromycin), is introduced into the stem cells under appropriate control such that expression of the gene occurs only in the desired cell lineage. For example, the marker gene can be under the control of a promoter which is active only in the desired cell lineage. Upon differentiation of the stem cells, the desired lineage is then selected based upon the marker, e.g. by contacting the mixed differentiated cells with the appropriate antibiotic to which the desired lineage has been conferred resistance. Cell lines other than the desired line will thus be killed, and a substantially pure, homogeneous population of the desired line can be recovered. In more preferred methods, two markers are introduced into the parent stem cells, one allowing selection of transfected stem cells from non-transfected cells, and one allowing selection of the desired cell lineage from other lineages. A double positive selection scheme can thus be used where each selectable marker confers antibiotic resistance. Using this selection methodology, populations comprised about 90% and even about 95–100% of the desired cell lineage can be obtained, as demonstrated in the Examples below.

To obtain grafts of the invention, the skeletal myoblasts or cardiomyocytes will be introduced into the myocardial tissue of a living animal such as a mammal. The cells can be introduced in any suitable manner, but it is preferred that the mode of introduction be as non-invasive as possible. Thus, delivery of the cells by injection, catheterization or similar means will be more desired.

The resulting graft-bearing animals have exhibited normal sinus rhythms, indicating that the graft per se, as well as the graft-host myocardium border zone, does not induce arrhythmias. This is in stark contrast to the remodeling that frequently occurs following infarcts in humans; the border zone of the infarct may give rise to circus loops which result in clinically significant arrhythmias (4, 5).

Grafts of the invention can be proliferative or non-proliferative. For example, the AT-1 grafts established in the specific Examples below are proliferative. On the other hand, the skeletal myoblast-derived grafts formed in the Examples are non-proliferative, with the absence of tritiated thymidine uptake demonstrating that the formation of stable intra-cardiac grafts was not dependent upon sustained cell proliferation.

Preferred grafts will be characterized by the presence of direct intracellular coupling and the formation of gap junctions between host and grafted cells. Moreover, such grafts will not cause immune response in the host, and will exhibit terminal differentiation of grafted cells and a non-tumorogenic nature.

Grafts of the invention are useful inter alia to deliver therapeutic proteins and the like via secretion from grafted cells, and to replace diseased or damaged tissue to supplement myocardial function. As examples of therapeutic protein deliveries, grafts may express angiogenic factors (as exemplified by basic and acidic Fibroblast Growth Factor; Transforming Growth Factor-Beta, Vascular Endothelial Growth Factor and Hepatocyte Growth Factor) to induce neovascularization. Similarly, grafts expressing neurotrophic agents near an infarcted region may be used to ameliorate the arrhythmogenesis associated with the border zone. These and many other candidate substances for targeted delivery to the heart will be apparent to those skilled in the area.

To promote a further understanding of the invention and its principles and advantages, the following specific Examples are provided. It will be understood that these Examples are illustrative, and not limiting, in nature.

EXAMPLE 1

Generation of Stable AT-1 Cardiomyocyte Grafts

A. Methods

AT-1 Cell Culture and Myocardial Grafting Protocol.

AT-1 cardiomyocytes were isolated from subcutaneous tumors by sequential collagenase digestion and cultured in PC-1 medium (Ventrex, Coon Rapids Minn.) containing 10% fetal calf serum as previously described in (6). Cells were labeled with 10 $\mu$M 8-chloromethyl-4,4-difluoro-1,3,5,7,-tetramethyl-4-bora-3a,4a-diazaindecene (BODIPY, Molecular Probes, Eugene Oreg.) for 30 min at 37° C. to facilitate localization of the injection site. Immediately before injection, cells were harvested with trypsin and collagenase, washed three times with serum-free PC-1 medium and directly injected into the ventricular myocardium of syngeneic B6D2/F1 mice (Jackson Laboratories, Bar Harbor Mass.) under open heart surgery as described in (7). Cells (4–10×10$^4$) were injected in a volume of 2–3 $\mu$l using a plastic syringe fitted with a 30 gauge needle.

Histology.

Hearts were removed following cervical dislocation and cryoprotected in 30% sucrose, embedded and sectioned at 10 $\mu$m with a cryomicrotome as described (8). For hematoxylin and eosin (H and E) staining, sections were post fixed in acetone:methanol (1:1) and stained according to manufacturer's specifications (Sigma Diagnostics, St. Louis Mo.). For immuno-histology, unfixed sections were reacted with polyclonal rabbit anti-T-Ag antibodies (either 161-T, see (3) or 162-T) followed by horseradish peroxidase-conjugated goat anti-rabbit antisera (Boehringer Mannheim, Indianapolis Ind.), and visualized by diaminobenzidine reaction with nickel enhancement as described in (9). Monoclonal antibodies against the common leukocyte antigen (CD45; antibody M1/9.3HL, Boehringer Mannheim) and against the macrophage Mac-1 antigen (CD11b; antibody M1/70HL, Boehringer Mannheim) were used to monitor intra-cardiac graft rejection. The Mac-1 antibody has 75–90% cross reactivity with lymphocytes. After treatment with primary antibody, sections were incubated with horseradish peroxidase-conjugated rabbit anti-rat antisera (Boehringer Mannheim), and visualized by diaminobenzidine reaction with nickel enhancement. For [$^3$H]-thymidine incorporation, mice were given a single bolus injection of isotope (400 $\mu$Ci at 28 Ci/mM, Amersham, Arlington Heights Ill.) and eighteen hours later sacrificed by cervical dislocation. The heart was removed, cryoprotected in 30% sucrose, embedded and sectioned with a cryomicrotome. Sections were post-fixed in methanol:acetone (1:1), stained with H and E, and a thin layer of photographic emulsion (Ilford L.4, Polysciences, Warrington Pa.) diluted 1:1 with distilled water was applied. Sections were exposed for 5–7 days at 4° C., and developed in Kodak D-19 at 20° C. for 4 minutes, washed with distilled water for 1 minute, fixed in 30% sodium thiosulfate for 10 minutes, and washed in distilled water.

Electron Microscopy (EM).

Tissue blocks were fixed in 2% glutaraldehyde in 0.1 M cacodylate buffer (pH 7.4) and post-fixed in 2% osmium tetroxide (Stevens Metallurgical Corp., New York N.Y.). All other EM chemicals were obtained from Ladd Research Industries, Inc. (Burlington Vt.). Tissue was stained en bloc with 2% uranyl acetate in pH 5.2 maleate buffer (0.05 M), dehydrated, and embedded in Ladd LX-112. Grafts were located using 1 $\mu$m sections stained with toluidine blue. After trimming, the block was thin sectioned, and stained with uranyl acetate and lead citrate. Specimens were viewed on a Phillips 400 transmission electron microscope.

Electrocardiogram (ECG) Analyses.

For surface ECG records, mice were anesthetized (2.5% Avertin, 0.015 ml/g body weight, IP, Fluka Chemicals, Lake Ronkomkoma N.Y.), surface electrodes were placed in the standard lead 1 position, and ECGs were recorded with a Narco Biosystems (Houston Tex.) high gain amplifier coupled to an A/D converter (Coulbourn Instruments, Lehigh Valley Pa.).

Plasma Enzyme Assay (PEA).

For lactate dehydrogenase (LDH) isoform assay, plasma was isolated by retro-orbital sinus bleeds under anesthesia (2.5% Avertin, 0.015 ml/g body weight, intraperitoneally (IP)). Plasma was fractionated on 1% agarose gels (CK Isoenzyme electrophoresis system, CIBA-Corning Diagnostics, Corning N.Y.) and the LDH isoforms visualized by a TNBT-Formazan histochemical assay (LDH Assay Kit, Sigma Diagnostics, St. Louis Mo.).

B. Results

In these studies, AT-1 cardiomyocytes (derived from transgenic animals that expressed the T-Ag oncoprotein in the heart) were injected directly into the myocardium of syngeneic mice and the viability of the grafted material was assessed. To facilitate localization of the injection site in preliminary experiments, AT-1 cardiocytes were incubated briefly with BODIPY prior to grafting. BODIPY is a nontoxic glutathione reactive dye which permits fluorescent tracking of living cells. The graft site was easily visualized by fluorescence microscopy using a FITC cube. Subsequent experiments did not utilize BODIPY.

Fifty percent (14/28) of the animals receiving AT-1 cardiomyocyte injections developed intra-cardiac grafts. In most instances, the grafts were neither encapsulated nor surrounded by scarred myocardium. At the level of light microscopy, grafted AT-1 cardiomyocytes were observed directly juxtaposed with host cardiomyocytes. The identity of the AT-1 cardiomyocytes was confirmed by immunoperoxidase assay using an anti-T-Ag antibody primary antibody (162-T) followed by a horseradish peroxidase conjugated secondary antibody. Specificity of the anti-T-Ag antibody has been established previously (10, 11). Black precipitate to was observed over cardiomyocyte nuclei in the graft but not in the host myocardium, confirming that the graft was comprised of AT-1 cardiomyocytes. Similar results were obtained with other anti-T-Ag antibodies, and no signal was observed in the absence of primary antibody.

Viable AT-1 cardiomyocytes were observed at least as long as four months post-implantation. During this period, some degree of graft proliferation occurred; $^3$[H]-thymidine incorporation analyses detected DNA synthesis in the grafted cells. Ten percent of the AT-1 cardiomyocyte nuclei were synthesizing DNA as evidenced by isotope incorporation into the nucleus. However, the rate was appreciably less than that observed for cultured AT-1 cardiomyocytes, where 50% of the cells synthesized DNA following a similar 3[H]-thymidine pulse. In several instances, the grafted AT-1 cardiomyocytes were localized within the subpericardial space.

Immunohistologic experiments were employed to determine if the intra-cardiac grafts were subject to chronic rejection. Grafts older than one month failed to react with antibodies specific for mouse leukocytes; signals observed in blood vessels located on the same section provided a positive control for the experiment. Similarly, an antibody which detects mouse macrophages and lymphocytes did not react with the intra-cardiac graft; once again positive signal was observed in a blood vessel located on the same section. Collectively, these results indicate the absence of chronic graft rejection by the syngeneic hosts. This result is supported by the observation that cyclosporine treatment (50 mg/kg body weight, administered intraperitoneally daily) did not influence significantly the frequency of intra-cardiac grafting (50% success rate, n=6). Sex of the host animal also did not appear to influence significantly the rate of graft formation (46% success rate in males, −n=13; 53% success rate in females, n=15). The frequency of grafting was similar in animals examined at early time points (1–40 days post-grafting, 47%, n=15) as compared to those examined at later time points (40–120 days post-grafting, 54%, n=13). Finally, similar frequencies of intra-cardiac grafting were observed when cells were delivered to either the left ventricular free wall or the apex of the heart.

Electron microscopic analysis of the AT-1 cardiomyocyte grafts confirmed the absence of encapsulation. High power views revealed well-developed junctional complexes between adjacent cells within the graft. Graft cardiomyocytes contained numerous polyribosomes and the dedifferentiated myofibrillar ultrastructure typical of AT-1 tumors in vivo (6). Electron-dense secretory granules were also observed in the AT-1 cardiomyocyte grafts, as would be expected for myocytes of atrial origin. Host cardiomyocytes bordering the grafts had normal ultrastructure with well-formed sarcomeres. Although only a thin basement membrane separated AT-1 and host cardiomyocytes, no junctional connections between these two cell types were observed.

Surface electrocardiograms were performed to determine if the presence of AT-1 cardiomyocyte grafts influenced the autonomic rhythm. No appreciable differences were observed between records from sham animals and those which harbored grafts. In each case, the experimental animals exhibited normal sinus rhythm, with an anesthetized heart rate of approximately 400 beats per minute. Normal P-QRS coupling was maintained, indicating that the grafted AT-1 cardiomyocytes did not act as an ectopic pacemaker. This latter result is important in light of the observation that AT-1 cardiomyocytes exhibit spontaneous electrical activity both in vivo (12) and in culture (3). The absence of overt arrhythmia also indicated that graft-induced myocardial remodeling was not associated with the generation of significant circus rhythms.

In addition to surface ECG, plasma LDH levels were assessed in mice carrying AT-1 cardiomyocyte grafts. The presence of the cardiac LDH isoform in the circulation is a well established hallmark of myocardial infarction. No cardiac LDH (isoform-1) was apparent in mouse plasma prior to grafting. After the introduction of AT-1 cardiomyocytes, there was a transient appearance of the cardiac isoform in the plasma, which most likely reflected damage to the host myocardium as well as damaged AT-1 cardiomyocytes. A transient increase in plasma skeletal LDH isoform was also observed following grafting surgery, presumably reflecting damage caused by the trans-thoracic incision. The plasma LDH profiles returned to normal by 7 days post-implantation. Thereafter, the plasma LDH profiles remained normal despite the presence of grafts.

EXAMPLE 2

Generation of Stable C2C12 Myoblast Grafts

A. Methods

C2C12 Cell Culture and Myocardial Grafting Protocol.

C2C12 myoblasts were obtained from ATCC. Cells were maintained in the undifferentiated state by culturing at low density in high glucose Dulbecco's Modified Eagle Media (DMEM) supplemented with 20% fetal bovine serum, 1% chicken embryo extract, 100 units/ml penicillin and 100 $\mu$g/ml streptomycin. For some studies, myogenic differentiation was induced by culturing in DMEM supplemented with 2% horse serum and antibiotics. Immediately before injection, myoblasts were harvested with trypsin, washed three times with serum free DMEM and directly injected into the ventricular myocardium of adult syngeneic C3Heb/FeJ mice (Jackson Laboratories) under open heart surgery as described in (7). Cells ($4-10\times10^4$ were injected in a volume of 2–3 $\mu$l using a plastic syringe fitted with a 30 gauge needle.

Histology.

Hearts were removed, cryoprotected, embedded and sectioned as in Example 1. H and E staining and [$^3$H]-thymidine incorporation assays were also conducted as in Example 1. For immunohistology, methanol fixed sections (–20° C., 10 min.) were reacted with the monoclonal anti-skeletal myosin heavy chain antibody (MY-32, Sigma Chemical Corp.) followed by rhodamine-conjugated sheep anti-mouse IgG F(ab')$_2$ fragment (Boehringer Mannheim), and visualized by epifluorescence.

Electron Microscopy.

EM was performed as in Example 1.

Electrocardiogram Analyses.

ECG anlyses were performed as in Example 1.

Plasma Enzyme Assay.

PEA was performed as in Example 1.

B. Results

Several myoblast cell lines are known which, as exemplified by C2C12 cells, have the capacity to differentiate into myotubes in culture (13). C2C12 myoblasts were derived from cultured explants of injured thigh muscle of C3H mice. When maintained in serum-rich media, the myoblasts proliferate rapidly and retain an undifferentiated phenotype. However, when cultured in serum-poor media myogenic differentiation is induced. The C2C12 cells withdraw from the cell cycle and fuse, thereby forming multinucleated myotubes. Myogenic differentiation is also induced, as evidenced by the appearance of numerous muscle-specific gene products. Thus, in this model proliferation and myogenic differentiation are mutually exclusive (14). Myoblast differentiation in vitro is thought to mimic satellite cell mediated myofiber regeneration in vivo.

Myoblasts were injected directly into the myocardium of syngeneic C3Heb/FeJ mice and the viability of the grafted material was assessed. One hundred percent (13/13) of the mice receiving intra-cardiac implants of C2C12 myoblasts developed grafts in the heart. Viable grafts were observed as long as six months post-implantation (this was the last time point assayed). In all instances, the grafted material was not encapsulated. The differentiated status of the grafted C2C12 cells was determined by immunohistological assay with an anti-myosin heavy chain antibody (MY-32). This antibody does not react with myoblasts nor with cardiac myosin heavy chain. Although differentiated C2C12 cells were observed in every heart receiving myoblast injections, the grafting efficiency of individual cells was not determined. As an additional control, hearts bearing AT-1 intra-cardiac grafts (see Example 1) were examined with the MY-32 antibody. No staining was observed, thereby ruling out the possibility that the signal seen in the C2C12 grafts was due to skeletal myosin heavy chain induction in host cardiomyocytes.

Example 1 above demonstrates that AT-1 cardiomyocytes form stable grafts in syngeneic myocardium. However, the observation that these cells retained the capacity for proliferation in vivo raised the possibility that sustained cell division might be required for successful intra-cardiac grafting. The proliferative status of the C2C12 grafts was therefore examined. Virtually no DNA synthesis (as assessed by tritiated thymidine incorporation) was observed, indicating that the majority of the grafted C2C12 cells had indeed withdrawn from the cell cycle. Examination of serial sections indicated that less than 0.1% of the cells in or near the grafts were synthesizing DNA. This result most likely reflects fibroblast proliferation during the remodeling process. As with the AT-1 grafts, immunohistological analyses of C2C12 grafts failed to detect macrophage, inflammatory leukocyte or lymphocyte infiltration at two months post-implantation, indicating the absence of chronic graft rejection by the syngeneic hosts.

At the level of light microscopy, the C2C12 intra-cardiac grafts exhibited cellular heterogeneity with both H and E and MY-32 immunofluorescence staining. Electron microscopic analyses were employed in an effort to further characterize the cellular make-up of the C2C12 grafts. Toluidine-stained 1 $\mu$m sections were surveyed at 100 $\mu$m intervals to locate graft sites for EM analysis. Once localized, thin sections were prepared from the block. Cells with morphology typical of skeletal myocytes were observed throughout the graft. Abundant mitochondria localized between well developed sarcomeres were readily detected. Prominent Z bands and thick and thin filaments were observed. Occasionally, expanded t-tubules and ruffled cell membranes were detected in the grafted myocytes. In addition to well developed myocytes, a second less differentiated cell type was observed in C2C12 grafts. Most notably, these cells exhibited a large nucleus to cytoplasm ratio, with a prominent band of heterochromatin at the nuclear periphery. Moderate amounts of centrally located heterochromatin were also detected. Limited rough endoplasmic reticulum and few mitochondria were observed in these cells. Similar ultrastructural characteristics have been ascribed to satellite cells in vivo and in culture (15, 16).

Two studies were initiated to assess any deleterious effects of C2C12 intra-cardiac grafts on host heart function. In the first study, surface electrocardiograms failed to detect any appreciable differences between records from control and experimental mice. All animals examined had normal P-QRS coupling, and exhibited normal sinus rhythm with an anesthetized heart rate of approximately 400 beats per minute. These data indicate that the intra-cardiac myoblast grafts did not induce overt cardiac arrhythmias. In the second study, plasma LDH levels were monitored in graft-bearing animals. The presence of the cardiac LDH isoform in the circulation is a well established hallmark of myocardial infarction. The cardiac-specific LDH isoforms (isoforms 1, 2, and 3) were not observed in plasma prior to grafting. Immediately after grafting, an increase in the cardiac isoforms was observed in plasma, which most likely reflected damage to the host myocardium. A transient increase in the plasma skeletal LDH isoform (isoform 5) was also observed, presumably reflecting damage caused by the trans-thoracic incision. Plasma LDII profiles returned to normal by 7 days post-implantation.

EXAMPLE 3

Generation of Stable Fetal Cardiomyocyte Grafts

A. Methods

Cardiomyocyte Cell Culture and Myocardial Grafting Protocol.

Figure 1:
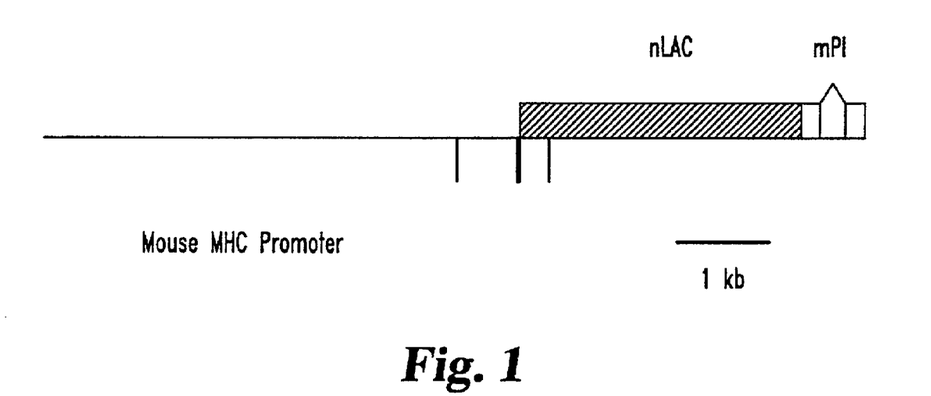
FIG. 1 is a schematic diagram illustrating DNA used to generate MHC-nLAC transgenic mice in Example 3, infra.

Transgenic mice were generated which carry a fusion gene comprised of the α-cardiac myosin heavy chain (MHC) promoter and a modified β galactosidase (nLAC) reporter. To generate the MHC-nLAC transgenic mice, MHC-nLAC insert DNA (see FIG. 1) was purified by absorption onto glass beads, dissolved at a concentration of 5 µg/ml, and microinjected into the nuclei of one cell inbred C3H3B/FeJ embryos according to established protocols (17). Polymerase Chain Reaction (POR) analysis was employed to identify founder animals and to monitor transgene segregation. The sense strand primer 5'-GGTGGG-GGCTCTTCACCCCCAGACCTCTCC-3' (SEQ ID No. 1) was localized to the MHC promoter and the antisense strand primer 5'-GCCAGGGTTTTCCCAGTCACGACGTTGT-3' (SEQ ID No. 2) was localized to the nLAC reporter. PCR analyses were as described in (18). The MHC promoter consisted of 4.5 kb of 5' flanking sequence and 1 kb of the gene encompassing exons 1 through 3 up to but not including the initiation codon. The nLAC reporter was modified so as to carry both a eukaryotic translation initiation site and the SV40 nuclear localization signal (19). The mP1 sequences carried an intron, as well as transcriptional termination and polyadenylation signals from the mouse protamine 1 gene.

For preparations for examination of β galactosidase (BGAL) activity and DAPI epifluorescence, transgenic animals were heparinized (10,000 U/kg IP) prior to sacrifice by cervical dislocation. Hearts were placed in a beaker of gassed (95% $O_2$ 5% $CO_2$) KHB buffer (105 mM NaCl, 20 mM $NaHCO_3$, 3.8 mM KCl, 1 mM $KH_2 PO_4$, 1.2 mM $MgSO_4$, 0.01 mM $CaCl_2$, 1 mM mannitol, 10 mM taurine, 10 mM dextrose, 5 mM Na-pyruvate). Hearts were then hung by the aorta and perfused with gassed KHB (0.5 ml/min at 37° C.) containing 2.5 mM EGTA for five minutes, followed by 0.17% collagenase (Type I, Worthington Biochemical, Freehold N.J.) in KHB. Hearts were perfused until flaccid and the ventricles were minced with scissors and isolated cells obtained by triturating with a Pasteur pipette. After at least one hour of formalin fixation, suspensions were filtered and smeared onto positively charged slides (Superfrost Plus, Fisher, Pittsburgh Pa.), and allowed to dry.

For isolation of single cells for injection, females with 15 day embryos (onset of pregnancy determined by vaginal plugs) were sacrificed by cervical dislocation. Embryos were removed, decapitated, and hearts were harvested under PBS, and ventricles and atria were separated. Transgenic ventricles (identified by cardiac BGAL activity) were digested in 0.1% collagenase (Worthington) in DPBS (Dulbecco's Phosphate Buffered Saline, Sigma) for 45 minutes, and were triturated with a Pasteur pipette in PC-1 medium (Ventrex, Coons Rapids Minn.) with 10% FBS, resulting in a suspension of single cells.

Immediately after isolation, embryonic cardiomyocytes were washed three times with DPBS and directly injected into the ventricular myocardium of syngeneic mice (Jackson Laboratories) under open heart surgery as in Example 1. $1-10\times10^4$ cells were injected in a volume of 2–3 µl using a plastic syringe fitted with a 30 gauge needle.

Histology.

For H and E, X-GAL, immunohistology and thymidine analyses, hearts were removed following cervical dislocation and cryoprotected in 30% sucrose, embedded and sectioned at 10 µm with a cryomicrotome as in Example 1. H and E staining, monitoring for intra-cardiac graft rejection, and assay for [$^3$H]-thymidine incorporation were also conducted as in Example 1. To assay βGAL activity, sections were hydrated in PBS, post-fixed in acetone:methanol (1:1) and then overlaid with mixture containing 1 mg/ml X-GAL (5-bromo-4-chloro-3-indolyl-B-D-galactoside), 5 mM potassium ferricyanide, 5 mM potassium ferrocyanide and 2 mM magnesium chloride in PBS. Positive staining is indicated by the appearance of a blue chromophore. After treatment with primary antibody, signal was visualized by an avidin-biotin (ABC) kit (Vector Labs, Burlingame Calif.). The heart was processed as described above, and sections were post-fixed in methanol:acetone (1:1), stained with H and E, and coated with a thin layer of photographic emulsion (Ilford L.4, Polysciences) diluted 1:1 with distilled water. Sections were exposed, developed, washed, fixed and washed as in Example 1. X-GAL staining of single cell preparations was as described above. For visualization of nuclei in single cell preparations, slides were stained with DAPI in PBS (0.28 µM, three min. at room temperature, Boehringer Mannheim), washed three times in PBS, and wet-mounted in 2% propyl gallate dissolved in glycerol. To obtain coronal heart sections, mice were sacrificed by cervical dislocation, hearts were harvested and perfused on a Langendorff apparatus with 2% glutaraldehyde in 0.1 M cacodylate buffer (pH 7.4). After immersion fixation overnight in the same buffer, 200 µm coronal sections were made with a vibratome (Campden, London, United Kingdom). To localize the graft, sections were pooled and stained for βGAL activity with X-GAL as described above.

Electron Microscopy.

MHC-nLAC embryonic grafts were localized in coronal heart sections as described above. After trimming, the tissue was post-fixed in 2% osmium tetroxide (Stevens Metallurgical Corp., New York N.Y.). Tissue was then dehydrated and embedded in Ladd LX-112 (Ladd Research Industries). Grafted areas were further trimmed, thin sectioned, and stained with uranyl acetate and lead citrate. Specimens were viewed on a Phillips 400 transmission electron microscope as in Example 1.

Electrocardiogram Analyses.

ECG analyses were conducted as in Example 1.

B. Results

Transgenic mice generated as above carried a fusion gene comprised of the MHC promoter and a nLAC reporter. nLAC carries the SV40 nuclear transport signal, which results in the accumulation of β galactosidase activity in the nucleus of targeted cells. Four transgenic lineages were produced, and two (designated MHC-nLAC-2 and MHC-nLAC-4) were selected for further analyses. To ensure that the MHC-nLAC transgene would provide a suitable cell lineage marker, β galactosidase (βGAL) activity was assessed in transgenic cardiomyocytes. Single cell preparations generated by retrograde collagenase perfusion were examined simultaneously for BGAL activity and DAPI epifluorescence. 99.0±0.45% (n=400) of the transgenic cardiomyocyte nuclei expressed ⊕GAL, whereas no βGAL activity was detected in noncardiomyocytes. In addition, no nuclear BGAL activity was detected in nontransgenic control cardiomyocytes.

Single cell suspensions were prepared by collagenase digestion of hearts harvested from embryonic day 15 transgenic mice. Greater than 95% of the cardiomyocytes isolated by this technique were viable as evidenced by dye exclusion assay. Cardiomyocytes were delivered to left ventricular free wall of syngeneic nontransgenic animals. Grafted cardiomyocytes were readily and unambiguously identified by virtue of the nuclear BGAL activity encoded by the MHC-nLAC transgene. Grafted cardiomyocytes were frequently observed at sites distal to the point of delivery; it presently is not clear if this distribution of grafted cells reflects cardiomyocyte migration or passive diffusion along dissection planes produced by the injection process. Approximately 50% (7/13) of the animals receiving intra-cardiac injections of embryonic cardiomyocytes developed grafts. This frequency of successful graft formation is likely to increase as cell preparation and implantation protocols are optimized.

Light microscopic analyses of H and E stained sections processed for βGAL activity indicated that grafted cardiomyocytes (blue nuclei) were juxtaposed directly with host cardiomyocytes (purple nuclei). Additional H and E analyses failed to detect significant graft encapsulation. The observed proximity of graft and host cardiomyocytes and absence of encapsulation are prerequisites for successful coupling between the two cell types.

Consecutive sections of a 19 day old intra-cardiac graft were processed for H and E, βGAL activity, and macrophage and leukocyte immunoreactivity. No evidence for graft rejection was observed, despite the fact that the animals were not immune suppressed. As a positive control for the immunohistology, grafts of incompatible MHC haplotype were produced; graft rejection was clearly evident in these hearts. Tritiated thymidine uptake analyses indicated that only 0.6% (n=156) of the βGAL-positive nuclei were synthesizing DNA, although noncardiomyocyte DNA synthesis was apparent. Since the embryonic day 15 donor cells were still mitotically active when grafted (labeling index of ca. 29%), the exceedingly low level of DNA synthesis observed in βGAL positive cells at 19 days post-grafting suggested that the MHC-nLAC embryonic cardiomyocytes had undergone terminal differentiation.

The juxtaposition of graft and host cardiomyocytes observed by light microscopic analyses prompted a determination whether direct intercellular coupling could be detected between the two cell types. The X-GAL reaction product is an electron-dense precipitate which can be detected by transmission electron microscopy (TEM, see 19). Vibratome sections from glutaraldehyde perfusion-fixed hearts were stained for βGAL activity, and grafted regions talus identified were trimmed and embedded for TEM. βGAL positive nuclei were readily observed by light microscopic analysis of 1 μm sections. The X-GAL reaction product had a perinuclear appearance due to a slight degree of nuclear leaching which occurred during the embedding process. The same groups of cardiomyocytes were identified by TEM analysis of a consecutive thin section. Host cardiomyocytes, which were not readily identified in the light micrographs due to the absence of perinuclear BGAL activity, were observed by electron microscopy to be juxtaposed with the grafted cells. Numerous junctional complexes were present between the host and graft cardiomyocytes, indicating a high degree of intercellular coupling. Many examples of intercellular coupling between host and graft cardiomyocytes were observed throughout the grafted regions. Importantly, intercellular connections could be traced from βGAL positive cardiomyocytes through numerous host cells, thus demonstrating that grafted cardiomyocytes could be participating in a functional syncytium.

In addition to documenting the presence of abundant intercellular coupling between grafted and host cardiomyocytes, the TEM analyses revealed that the grafted cardiomyocytes were highly differentiated. Normal characteristics of adult cardiomyocytes were observed including myofibrillae forming complete sarcomeres, numerous junctional complexes between cells and abundant mitochondria. Indeed, aside from the presence of the X-GAL reaction product, grafted cardiomyocytes were indistinguishable from host cells. Further, binucleated, βGAL positive cells could be detected in the intra-cardiac grafts. Because binucleation is a characteristic of adult rodent cardiomyocytes, this observation further supports that the grafted cardiomyocytes have undergone terminal differentiation.

Surface ECG recordings were employed to determine-if the presence of coupled embryonic cardiomyocyte grafts negatively influenced host heart automaticity. ECG traces from graft-bearing animals were indistinguishable from sham operated controls, and exhibited P and QRS complexes typical for mice. There was no evidence for cardiac arrhythmia in graft-bearing animals, despite the presence of a high degree of intercellular coupling between grafted and host cardiomyocytes.

EXAMPLE 4

Preparation of Substantially Pure Cardiomyocyte Culture

Embryonic stern cells were genetically modified in a manner enabling the production of a substantially homogeneous population of non-immortalized cardiomyocytes. The parental ES cell line (D3) was cotransfected with a pGK-HYG (hygromycin) plasmid and a plasmid containing a MHC-neo$^r$ gene. The pGK-HYG plasmid provides selection for transfected ES cells, while the mMHC-neo$^r$ gene facilitates a second round of selection on differentiated cells: incubation in the presence of G418 eliminates non-cardiomyocytes (that is, cells in which the MHC promoter is not active).

Stably tranfected ES cells were selected by growth in the presence of hygromycin. The plasmids were linearized and introduced into the stem cells via electroporation at 1180 μFarad, 220 volts. The transfected cells were maintained in DMEM supplemented with 10% preselected FBS, 0.1 mM β-mercaptoethanol, nonessential amino acids, PenStrep and LIF, and transformants selected by the addition of hygromycin into the medium. Co-transfectants were then identified by PCR analysis specific for both transgenes. The transfections produced a cell line, designated 9A, which carries both transgenes.

Cardiogenesis was induced in 9A ES cells by plating 2×10⁶ cells onto uncoated 100 mm bacterial petri dishes in the absence of LIF. After 8 days in culture, numerous patches of cells exhibiting spontaneous contractile activity (i.e. cardiomyocytes) were observed. At this point, G418 was added to the media, and the cells incubated for an additional 9 days. During this treatment it was apparent that many of the non-cardiomyocytes were being killed by the G418. Importantly, the G418 had no discernible effects on the cardiomyocytes, which retained their spontaneous beating activity throughout the course of the experiment.

After a total of 9 days of G418 selection, the surviving cells were dissociated with collagenase and trypsin, and then replated onto fibronectin coated microscope slides. The cells were cultured an additional 24 hours to allow them to recover from passage, and then fixed for immunocytologic analysis. Cells were reacted with MF20, a monoclonal antibody which recognizes sarcomeric myosin. Cells were then individually counted for the presence or absence of sarcomeric myosin, a marker for cardiomyocytes. The results were as follows:

| | |
|---|---|
| Total number of cells counted: | 794 |
| Number of MF20+ cells: | 791 |
| Number of MF20− cells: | 3* |
| Percent cardiomyocytes: | 99.6% |

*The 3 cells which did not stain with MF20 may still have been cardiomyocytes, since this antibody will not react with monomeric myosin.

It was thus demonstrated that the expression of drug (neomycin) resistance under a cardiac-specific promoter enables the selection of an essentially pure population of ES derived cardiomyocytes in culture. Such populations can be used to form myocardial grafts using procedures as discussed in the Examples above.

EXAMPLE 5

Delivery of Protein via Graft

A. Methods

C2C12 Cell Culture and Transfection.

C2C12 myoblasts (ATCC) were maintained in the undifferentiated state by culturing at low density in high glucose Dulbecco's Modified Eagle Media (DMEM) supplemented with 20% fetal bovine serum, 1% chicken embryo extract, 100 units/ml penicillin and 100 µg/ml streptomycin. For some studies, myogenic differentiation was induced by culturing in DMEM supplemented with 2% horse serum and antibiotics.

A fusion gene comprised of the metallothionein (MT) promoter driving a modified Transforming Growth Factor-Beta 1 (TGF-β1) cDNA was obtained from Samuel and colleagues (20). Transcriptional activity of the metallothionein promoter can be regulated by modulating the heavy metal content of cell culture media. The TGF-β1 cDNA carried site-directed mutations which resulted in the conversion of $Cys^{223}$ and $Cys^{225}$ to serines. This modification (described further in (21)) results in the elaboration of a TGF-β1 molecule which is unable to form dimers, and consequently is not subject to normal post translational regulation. Cells expressing the modified cDNA constitutively secrete processed, active TGF-β1 (20). The MT-TGF fusion gene was introduced into C2C12 myoblasts by calcium phosphate transfection; stable transfectants were selected by virtue of co-transfection with an SV40-neo$^r$ transgene. Four independent clones were isolated, and presence of the transgene was confirmed by Southern blot analysis. The relative levels of TGF-β1 expression in the different clonal cell lines was initially assessed by Northern blot analysis, and one line, designated C2(280), was utilized for subsequent experiments.

Myocardial Grafting Protocol.

The grafting protocol was as described in Example 1. Fourteen days post-surgery, graft bearing animals were given heavy metal (25 mM $ZnSO_4$ in drinking water). Zinc treatment was continued until the termination of the experiment (1–4 weeks).

Histology.

For paraffin sections, hearts were fixed in 10% neutral buffered formalin, dehydrated through graded alcohols, and infiltrated with paraffin. Tissue blocks were then sectioned at 6 µm. H and E staining was performed directly after sectioning according to manufacturer's specifications (Sigma Diagnostics).

For [³H]-thymidine incorporation, mice were given a bolus and sacrificed as in Example 1. The heart was removed and processed for paraffin embedding as described above. Autoradiography was likewise conducted as in Example 1.

B. Results

Expression of recombinant TGF-β1 in response to heavy metal induction was examined in C2(280) myoblasts and myotubes. Transgene transcripts (1.8 kb) were readily distinguished from those originating from the endogenous TGF-β1 gene (2.5 kb) by Northern blot analysis. Addition of heavy metal to the culture media resulted in a marked increase of recombinant TGF-β1 transcripts in C2(280) myoblasts and myotubes. As indicated above, modified TGF-β1 expressed by C2(280) cells should have constitutive biological activity. To directly test this, conditioned media from C2(280) myoblasts and myotubes was examined by growth inhibition assay.

C2(280) myoblasts were used to produce intra-cardiac grafts in syngeneic C3Heb/FeJ mice. The presence of grafts was readily detected in H and E stained sections. 100% (n>50) of the animals receiving intra-cardiac injections of C2(280) cells went on to develop grafts. Interestingly, H and E analysis suggested that the C2(280) grafts were somewhat less differentiated as compared to those produced with unmodified C2C12 cells. This result was confirmed by immunohistologic analysis with a monoclonal antibody which recognizes skeletal myosin heavy chain.

C2(280) graft transgene expression was assessed by immunohistology with an anti-TGF-β1 antibody; TGF-β1 expression was readily detected in C2(280) grafts. As a negative control, TGF-β1 expression was assessed iii grafts produced by C2C12 myoblasts. As expected, the relative levels of TGF-β1 expression were markedly reduced in C2C12 grafts as compared to C2(280) grafts.

TGF-β1 is a well known angiogenic factor. ³H-thymidine incorporation analyses in vascular endothelial cells was therefore assessed to determine if an enhanced angiogenic response occurred in grafts expressing the MT-TGF transgene. DNA synthesis in vascular endothelial cells was readily apparent in C2(280) grafts under administration of a single bolus injection of ³H-thymidine (H-THY). In contrast, vascular endothelial DNA synthesis was markedly reduced in non-transfected C2C12 grafts (Table 1). To rule out the possibility that the angiogenic responses was due solely to graft mass, $^3$H-thymidine incorporation was compared between similar size and aged C2C12 and C2(280) grafts (Table 1). A marked increase in the number of vascular endothelial cells synthesizing DNA was apparent in all of the analyses. Finally, the thymidine incorporation assay also revealed that a percentage of the grafted myoblasts continued to proliferate. This observation is consistent with the known inhibitory effect of TGF-β1 on myodifferentiation, and most likely accounts for the undifferentiated appearance of the C2(280) grafts.

TABLE 1

TGF-β1 Delivery and
Vascular Endothelial DNA Synthesis

| Time Post Zn Induction | | C2C12 TGF-β1 (−) | C2 (280) TGF-β1 (+) |
|---|---|---|---|
| 1 Week | Total # $^3$H-THY + Endothelial Cells | 0 | 8 |
| | Total # of Vessel Sections Counted | 35 | 17 |
| | # Synthetic Cells/ Vessel Section | 0.0 ± 0.00 | 0.46 ± 0.036 |
| 2 Weeks | Total # $^3$H-THY + Endothelial Cells | 1 | 7 |
| | Total # of Vessel Sections Counted | 18 | 21 |
| | # Synthetic Cells/ Vessel Section | 0.06 ± 0.056 | 0.34 ± 0.052 |

While the invention has been illustrated and described in detail in the foregoing description, the same is to be considered as illustrative and not restrictive in character, it being understood that only the preferred embodiments have been described and that all modifications that come within the spirit of the invention are desired to be protected.

REFERENCES

The following references, to the extent that they provide exemplary procedural or other details supplementary to those set forth herein, are specifically incorporated herein by reference.

1. Tompson, L. Fetal transplants show promise. Science 257:868–870, 1992.
2. Gussoni, E., Pavlath, G. K., Lanctot, A. M., Sharma, K. R., Miller, R. G., Steinman, L. and Blau, H. M. Normal dystrophin transcripts detected in Duchenne muscular dystrophy patients after myoblast transplantation. Nature 356:435–438, 1992.
3. Steinhelper, M. E., Lanson, N., Dresdner, K., Delcarpio, J. B., Wit, A., Claycomb, W. C. and Field, L. J. Proliferation in vivo and in culture of differentiated adult atrial cardiomyocytes from transgenic nice. American Journal of Physiology 259 (Heart and Circulatory Physiology 28): H1826–H1834, 1990.
4. Janse, M. J., Cinca, J., Morena, H., Fiolet, J. W., Kleber, A. G., deVries, G. P., Becker, A. E. and Durrer, D. The border zone in myocardial ischemia. An electrophysiological, metabolic and histochemical correlation in the pig heart. Circulation Research 44:576–588, 1979.
5. Spear, J. F., Michelson, E. L., and More, E. N. Cellular electrophysiologic characteristics of chronically infarcted myocardium in dogs susceptible to sustained ventricular tachyarrhythmias. Journal of the American College of Cardiology 4:1099–1110, 1983.
6. Delcarpio, J. B., Lanson, N. A. Jr., Field, L. J. and Claycomb, W. C. Morphological characterization of cardiomyocytes isolated from a transplantable cardiac tumor derived from transgenic mouse atria (AT-1 cells). Circulation Research 69:1591–1600, 1991.
7. Rockman, H. A., Ross, R. A., Harris, A. N., Knowlton, K. U., Steinhelper, M. E., Field, L. J., Ross, J. Jr. and Chien, K. R. Segregation of atrial-specific and inducible expression of an ANF transgene in an in vivo murine model of cardiac hypertrophy. Proc. Natl. Acad. Sci. USA 88:8277–8281, 1991.
8. Bullock, G. R. and Petrusz, P., in Techniques in Immunocytochemistry, Vol. II, Academic Press, New York, 1983.
9. Field, L. J. Atrial natriuretic factor-SV40 T antigen transgenes produce tumors and cardiac arrhythmias in mice. Science 239:1029–1033, 1988.
10. Katz, E., Steinhelper, M. E., Daud, A. Delcarpio, J. B., Claycomb, W. C. and Field, L. J. Ventricular cardiomyocyte proliferation in transgenic mice expressing α-Cardiac Myosin Heavy Chain-SV40 T antigen fusion genes. American Journal of Physiology 262 (heart and Circulatory Physiology 31):H1867–1876, 1992.
11. Steinhelper, M. E. and Field, L. J. "SV40 large T-Antigen induces myocardiocyte proliferation in transgenic mice", in The development and regenerative potential of cardiac muscle, John Oberpriller and Jean Oberpriller, eds. Harwood Academic press, 1990.
12. Steinhelper, M. E. and Field, L. J. Cardiac Tumors and dysrhythmias in transgenic mice. Toxicologic Pathology 18: 464–469, 1990.
13. Yaffe, D., and O. Saxel. Serial passaging and differentiation of myogenic cells isolated from dystrophic mouse muscle. Nature 270:725–727, 1977.
14. Nadal-Ginard, B. Committment, fusion, and biochemical differentiation of a myogenic cell line in the absence of DNA synthesis. Cell 15:885–864, 1978.
15. Bruni, C. Mitotic activity of muscle satellite cells during the early stages of rhabdomyosarcomas induction with nickel subsulfide. In Muscle Regeneration, A. Mauro, editor. Raven Press, New York, N.Y., 1979.
16. Rubin, L. L., C. E. Keller and S. M. Schuetze. Satellite cells in isolated adult muscle fibers in tissue culture. In Muscle Regeneration, A. Mauro, editor. Raven Press, New York, N.Y., 1979.
17. B. Hogan, F. Costantini and E. Lacy, in Manipulating the Mouse Embryo—A Laboratory Manual, Cold Spring Harbor Laboratory Press, Cold Spring Harbor, N.Y., 1986.
18. M. E. Steinhelper, K. L. Cochrane and L. J. Field. Hypotension in transgenic mice expressing atrial natriuretic factor fusion genes. Hypertension 16:301–307, 1990.
19. A. D. Loewy, P. C. Bridgman and T. C. Mettenleiter. Brain Research 555:346, 1991.
20. S. K. Samuel, et al. Autocrine induction of tumor protease production and invasion by a metallothionein-regulated TGF-beta 1 (Ser223,225). Embo Journal [JC:emb] 11(4):1599–1605, 1992.
21. A. M. Brunner, et al. Site-directed mutagenesis of cysteine residues in the pro region of the transforming growth factor beta 1 precursor. Expression and characterization of mutant proteins. Journal of Biological Chemistry 264(23):13660–13664, 1989.
22. E. J. Robertson. Embryo-derived stem cell lines, in Teratocarcinomas and embryonic stem cells: a practical approach, E. J. Robertson, editor. IRL Press, Washington D.C., 1987.

What is claimed is:

1. A method for cellular grafting in myocardial tissue of an animal, comprising forming a stable cellular graft in myocardial tissue of an animal, wherein said graft contains engrafted myoblast cells, engrafted skeletal myocyte cells derived from the myoblast cells, or a combination thereof, and wherein the engrafted cells are viable for at least six months.

2. A method for cellular grafting according to claim 1, wherein the animal is a mammal.

3. A method for cellular grafting according to claim 2, wherein the myocardial tissue is diseased or damaged myocardial tissue.

4. A method for cellular grafting according to claim 3, wherein the myocardial tissue is infarcted tissue.

5. A method for cellular grafting according to claim 3, wherein the myocardial tissue is ventricular myocardial tissue.

6. A method for cellular grafting according to claim 5, wherein the myocardial tissue is left ventricular myocardial tissue.

7. A method for cellular grafting according to claim 1, wherein the engrafted cells are substantially non-immunogenic to the animal.

8. A method for cellular grafting according to claim 1, wherein the engrafted cells carry a transgene encoding a recombinant molecule.

9. A method for cellular grafting according to claim 1, wherein the recombinant molecule is a protein.

10. A method for cellular grafting according to claim 9, wherein the protein is delivered to the myocardial tissue by the engrafted cells.

11. A method for cellular grafting according to claim 10, wherein the protein is an angiogenic factor or neurotrophic agent.

12. A method for cellular grafting according to claim 11, wherein the protein is an angiogenic factor that induces neovascularization in the myocardial tissue.

13. A method for cellular grafting according to claim 12, wherein the angiogenic factor is basic or acidic Fibroblast Growth Factor, Transforming Growth Factor-Beta, Vascular endothelial Growth Factor, or Hepatocyte Growth Factor.

14. A method for cellular grafting according to claim 13, wherein the protein is a neurotrophic agent.

15. A method for cellular grafting according to claim 1, wherein the engrafted cells comprise skeletal myocyte cells.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 30
        (B) TYPE: Nucleotide Sequence
        (C) STRANDEDNESS: Single
        (D) TOPOLOGY: Linear (ii) MOLECULE TYPE: Primer (xi) SEQUENCE DESCRIPTION: SEQ ID NO: 1:

GGT GGG GGC TCT TCA CCC CCA GAC CTC TCC                                    30

(2) INFORMATION FOR SEQ ID NO: 2:

(i) SEQUENCE CHARACTERISTICS:
        (A) LENGTH: 28
        (B) TYPE: Nucleotide Sequence
        (C) STRANDEDNESS: Single
        (D) TOPOLOGY: Linear (ii) MOLECULE TYPE: Primer (xi) SEQUENCE DESCRIPTION: SEQ ID NO: 2:

GCC AGG GTT TTC CCA GTC ACG ACG TTG T                                      28